US00PP15596P2

(12) United States Plant Patent
Amorao et al.

(10) Patent No.: US PP15,596 P2
(45) Date of Patent: Mar. 1, 2005

(54) STRAWBERRY PLANT NAMED 'DRISCOLL CAMBRIA'

(50) Latin Name: *Fragaria×ananassa*
Varietal Denomination: Driscoll Cambria

(75) Inventors: Amado Q. Amorao, Camarillo, CA (US); Bruce D. Mowrey, Watsonville, CA (US); Michael Ferguson, Chatsworth, CA (US); Larry T. Kodama, Freedom, CA (US); JoAnne Coss, Salinas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 188 days.

(21) Appl. No.: 10/291,881

(22) Filed: Nov. 8, 2002

(51) Int. Cl.[7] ..... A01H 5/00
(52) U.S. Cl. ..... Plt./209
(58) Field of Search ..... Plt./209

*Primary Examiner*—Bruce R. Campell
*Assistant Examiner*—Michelle Kizilkaya
(74) *Attorney, Agent, or Firm*—Jones Day

(57) ABSTRACT

This invention relates to a new and distinct variety of strawberry named 'Driscoll Cambria'. The variety is similar to the varieties 'Ana Maria' and 'San Juan'. The variety is distinguished from 'Ana Maria' and 'San Juan', in particular, by its absence of bracts on leaves, weak glossiness of the leaves, globose growth habit, density of plants, very sparse stipule pubescence, upward petiole pose of hairs, predominantly cordate fruit shape, vary narrow band without achenes on fruit, and the fine texture of the fruit when tasted.

4 Drawing Sheets

Latin name of the genus and species of the plant claimed: The variety is botanically identified as *Fragaria×ananassa.*

1. BACKGROUND OF THE INVENTION

The new variety originated as a result of a controlled cross between the strawberry plants '61C117' (unpatented Driscoll variety) and '126B46' (unpatented Driscoll variety) in an ongoing breeding program, and was discovered in a controlled breeding plot in, Ventura County, Calif. in March 1998. The original seedling was asexually propagated by stolons in a nursery in Shasta County, Calif. Propagules were transplanted to a controlled breeding plot in Ventura, County, Calif. where it was identified and selected for further evaluation. 'Driscoll Cambria' was subsequently asexually propagated and underwent further testing at various locations in Monterey county, Calif. for three years. This propagation and testing has demonstrated that the combination of traits disclosed herein which characterize the new variety are fixed and retained true to type through successive generations of asexual reproduction.

2. SUMMARY OF THE INVENTION

The present invention relates to a new and distinct variety of strawberry named 'Driscoll Cambria'. The variety is botanically known as *Fragaria×ananassa.* The new variety is distinguished from other varieties by a number of characteristics as set forth in Tables 1 and 2.

3. COMPARISON TO SIMILAR VARIETIES

The varieties which we believe to be similar to 'Driscoll Cambria' from those known to use are 'Ana Maria' (U.S. Plant Pat. No. PP11,035, issued Aug. 17, 1999) and 'San Juan' (U.S. Plant Pat. No. PP12,899, issued Sep. 3, 2002). There are several characteristics of the new variety that are different from, or not possessed by 'Ana Maria', and 'San Juan'. The new variety has a diameter of inner calyx relative to outer on secondary flowers that is larger, sparse stipule and petiole pubescence, many stolons, the fruiting bodies have very narrow bands without achenes, a fine texture when tasted, and flowers in late-February.

'Driscoll Cambria' differs from its parent '61C117' (unpatented Driscoll variety) in several characteristics, including, but not limited to, being adapted to Northern California climate, where '61C117' is adapted to a Southern California climate. 'Driscoll Cambria' differs from its parent '126B46' (unpatented Driscoll variety) in several characteristics, including, but not limited to, having superior fruit shipability than '126B46'.

4. BRIEF DESCRIPTION OF THE DRAWINGS

The accompanying photographs show typical specimens of the new variety, including fruit, foliage and flowers, in color as nearly true as it is reasonably possible to make in color illustrations of these characteristics. The plants of 'Driscoll Cambria' characterized in the botanical description and depicted in the figures were grown outdoors in an annual production system. Measurements were taken during the late summer in the second half of the production season.

5. DESCRIPTION OF THE NEW VARIETY

Figure 1:
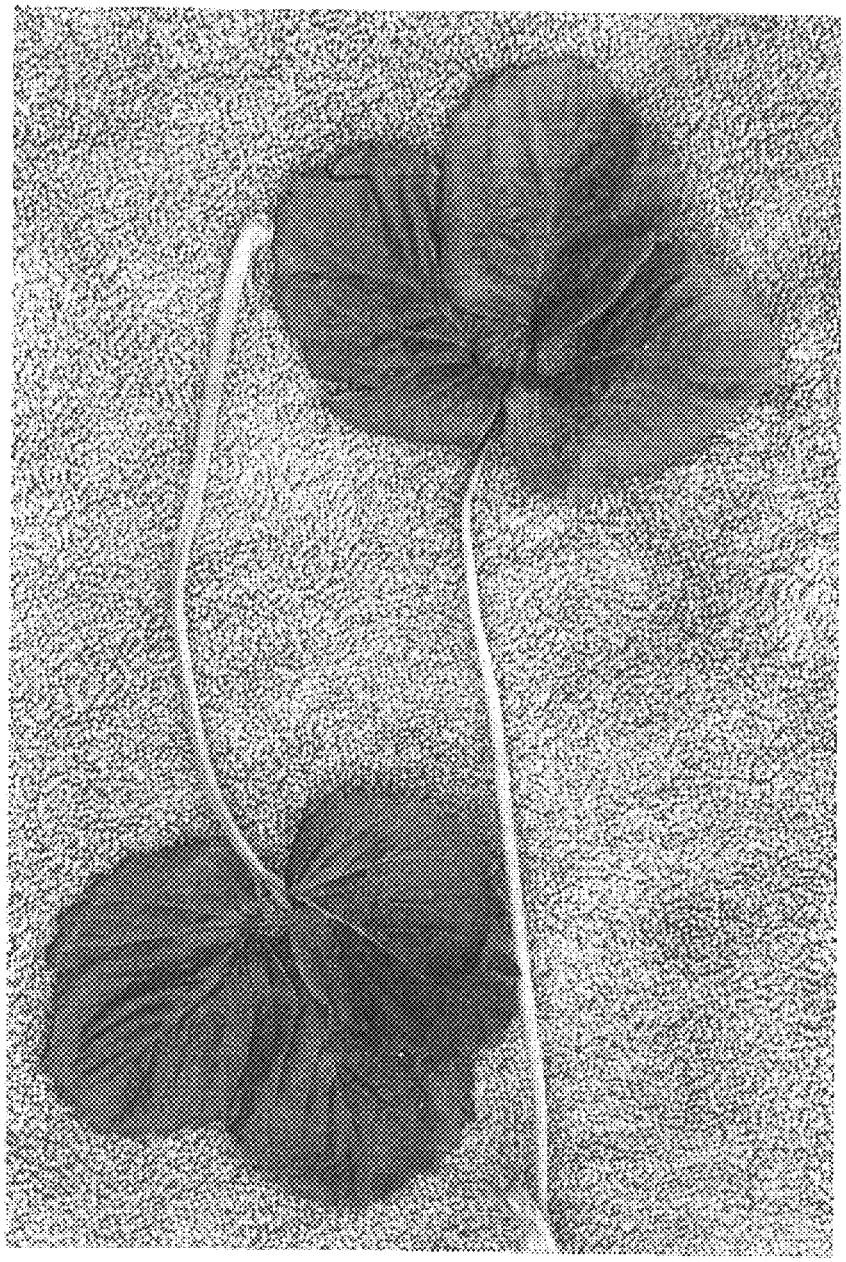
FIG. 1 shows leaves of the plant with three leaflets.
Figure 2:
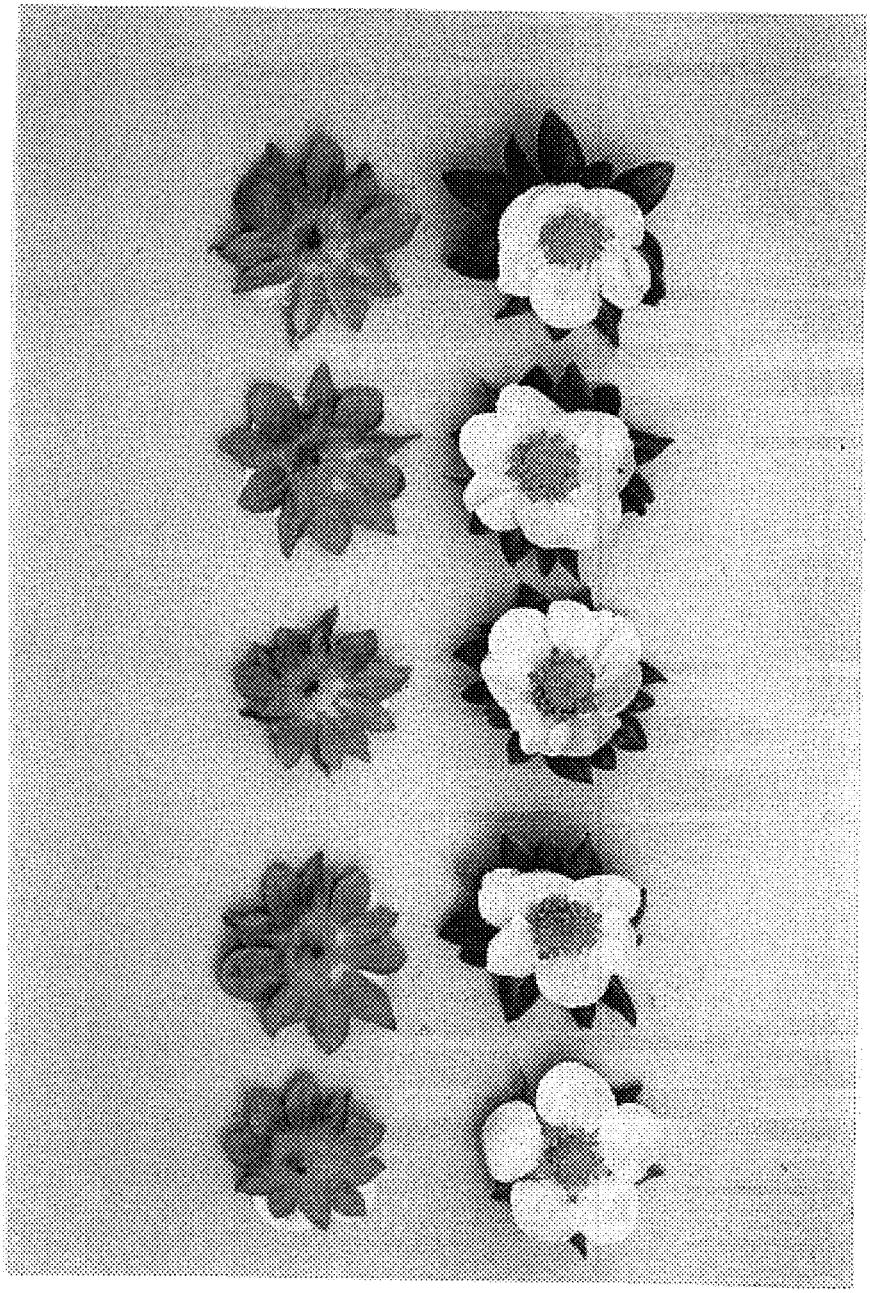
FIG. 2 shows the upper side and under side of the flowers.
Figure 3:
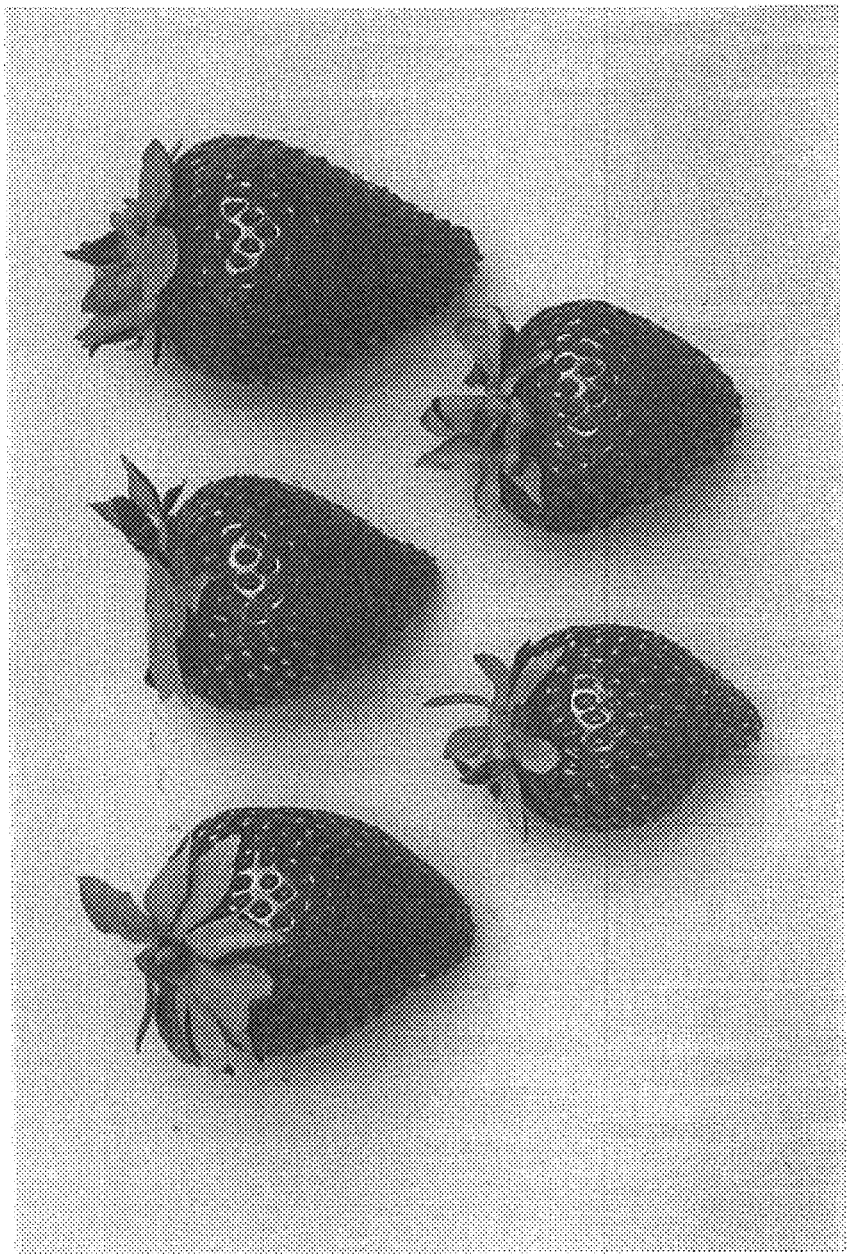
FIG. 3 shows a close-up of the strawberry.
Figure 4:
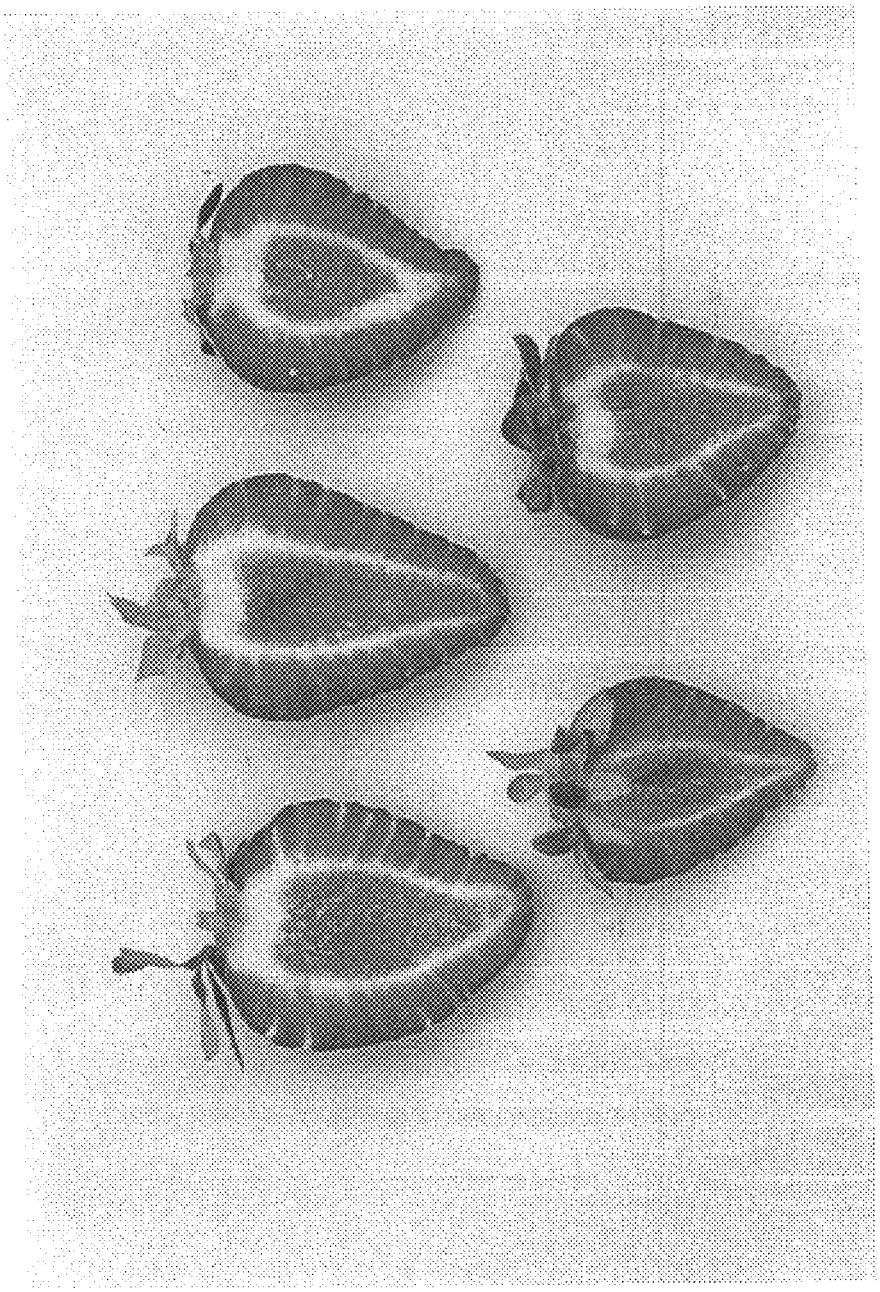
FIG. 4 shows the strawberry in longitudinal cross-section.

The following detailed description of the new variety is based upon observations taken of plants and fruit grown in Monterey county, Calif., U.S.A. Observations of 'Driscoll Cambria', 'Ana Maria' and 'San Juan' were taken in side by side comparison in 2002. This description is in accordance with UPOV terminology. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

5.1 PROPAGATION

The new variety is principally propagated by way of stolons. Although propagation by stolons is presently preferred, other known methods of propagating strawberry plants may be employed.

5.2 CHARACTERISTICS OF THE NEW VARIETY

Information on the new variety is presented in Tables 1, 2, 3 and 4. In the tables, the flowers described are secondary flowers except where indicated. The fruit described in the secondary fruit on one year old plants. Fruit and flower measurements are an average of both primary and secondary fruit and flowers. In particular, the reproductive structures of 'Driscoll Cambria' are fully self-fertile and typical of the species. Anther color in yellow, 13A, pistil color is yellow, 13A, and receptacle color is 150G, yellow green.

Table 1 provides information on the plant and fruit characteristics of the new variety 'Driscoll Cambria' compared with characteristics of 'Ana Maria' and 'San Juan'. Table 2 provides additional information of the plant and fruit characteristics of the new variety 'Driscoll Cambria' compared with characteristics of the varieties 'Ana Maria' and 'San Juan'. Table 3 provides reactions of the new variety to stresses, pests, and diseases as compared to the varieties 'Ana Maria' and 'San Juan'. Table 4 provides isozyme characteristics of the new variety as compared to the varieties 'Ana Maria' and 'San Juan'.

TABLE 1

QUANTITATIVE COMPARISON OF 'DRISCOLL CAMBRIA', 'ANA MARIA', AND 'SAN JUAN'

| | 'Driscoll Cambria' | 'Ana Maria' | 'San Juan' |
|---|---|---|---|
| Plant Characteristics | | | |
| Height of Plant (cm) | 28.3 | 33.6 | 30.1 |
| Spread of Plant (cm) | 41.7 | 51.8 | 47.1 |
| Number of Crowns | 4.2 | 4.3 | 3.8 |
| Leaf Characteristics | | | |
| Terminal Leaflet Length (cm) | 8.2 | 9.8 | 8.3 |
| Terminal Leaflet Width (cm) | 7.8 | 9.5 | 7.9 |
| Terminal Leaflet Length/Width Ratio | 1.05 | 1.03 | 1.05 |
| #Teeth/Terminal Leaflet | 18.8 | 21.3 | 24.6 |
| Color of upper side | light green 147A | medium green 147A | medium to dark green 147A |
| Color of under side | light green 147B | light green 148B | light green 147C |
| Petiole Length (cm) | 19.7 | 20.7 | 19 |
| Petiole Color | 149A | 145B | 149A |
| Bract Frequency | 0% | 67% typically single | 25% typically paired |
| Stipule Length (cm) | 3.5 | 3.4 | 3.6 |
| Stipule Width (cm) | 1.14 | 1.07 | 1.11 |

TABLE 1-continued

QUANTITATIVE COMPARISON OF 'DRISCOLL CAMBRIA', 'ANA MARIA', AND 'SAN JUAN'

| | 'Driscoll Cambria' | 'Ana Maria' | 'San Juan' |
|---|---|---|---|
| Flower Characteristics | | | |
| Petal Length (cm) | 1.07 | 1.29 | 1.05 |
| Petal Width (cm) | 1.13 | 1.22 | 1.10 |
| Petal Length/Width Ratio | 0.95 | 1.05 | 0.95 |
| Flower Diameter (cm) | 2.00 | 2.15 | 2.15 |
| Calyx Diameter (cm) | 2.86 | 3.07 | 2.91 |
| Fruiting Truss Length (cm) | 35.0 | 36.9 | 34.0 |
| Petal Color (cm) | 155D | 155D | 155C |
| Fruit Characteristics | | | |
| Fruit Length (cm) | 4.19 | 3.99 | 4.33 |
| Fruit Width (cm) | 3.41 | 3.74 | 3.85 |
| Fruit Length/Width Radio | 1.23 | 1.07 | 1.13 |
| Average Berry Weight (g) | 23.3 | 22.5 | 28.4 |
| Extenal Color | red 46A | red 46A | dark red 53A |
| Internal Color | orange red 41A | orange red 44B | red 44A |
| Average % brix | 11.0 | 8.34 | 8.97 |
| Brix/Acid Ratio | 15.35 | 13.48 | 15.07 |
| Achene Coloration | dark red to yellow 53A to 16A | dark red to yellow 46B to 16A | dark red to yellow 46B to 16A |
| Yield (g/plant) | 1,366 | 1,504 | 1,225 |

TABLE 2

QUALITATIVE COMPARISON OF 'DRISCOLL CAMBRIA', 'SAN JUAN' AND 'ANA MARIA'

| | 'Driscoll Cambria' | 'Ana Maria' | 'San Juan' |
|---|---|---|---|
| Plant | | | |
| Habit | globose | globose to upright | globose to flat globose |
| Density | dense | medium to open | medium |
| Vigor | strong | strong | medium |
| Leaf | | | |
| Shape in cross section | concave | slightly concave to flat | flat to slightly convex |
| Interveinal blistering | strong | medium to strong | medium to strong |
| Glossiness | weak | medium | weak to medium weak |
| Number of leaflets | three only | three only | sometimes more than 3 leaflets (approx. 17% of leaves) |
| Terminal teaflet margin profile | flat | flat | revolute to flat |
| Terminal leaflet shape of base | rounded | rounded to oblique | obtuse to rounded |
| Terminal leaflet shape of teeth | rounded | obtuse | rounded |
| Stipule pubescence | very sparse | sparse | medium dense |
| Petiole pubescence | very sparse | sparse | medium |
| Petiole pose of hairs | upwards | outward | outward to downward |

TABLE 2-continued

QUALITATIVE COMPARISON OF 'DRISCOLL CAMBRIA', 'SAN JUAN' AND 'ANA MARIA'

| | 'Driscoll Cambria' | 'Ana Maria' | 'San Juan' |
|---|---|---|---|
| Stolon | | | |
| Amount | many | medium to many | medium to many |
| Anthocyanin coloration | medium | medium | strong |
| Thickness | thick | thin to medium | medium |
| Pubescence | medium | sparse to medium | medium |
| Inflorescence | | | |
| Position relative to foliage | level to above | level to above | beneath to level with |
| Diameter of calyx relative to corolla on secondary flowers | same size on secondary flowers, larger on primary flowers | smaller to same size | larger |
| Diameter of inner calyx relative to outer on secondary flowers | larger | smaller to same size | same size |
| Spacing of Petals | overlapping | free to touching | overlapping |
| Fruiting Truss | | | |
| Attitude at first picking | prostate | semi-erect | prostate |
| Fruit | | | |
| Predominant shape | cordate | conical | conical to almost cylindrical |
| Difference in shapes between primary and secondary fruits | slight | none to very slight | moderate |
| Band without achenes | very narrow | narrow to medium | narrow |
| Unevenness of surface | very weak | weak | mean |
| Evenness of color uneven | even | even | even |
| Glossiness | strong | strong | very strong |
| Insertion of achenes | level with surface | level with surface | level with surface |
| Insertion of calyx | level | level with to set above | level |
| Pose of the calyx segments | spreading to reflexed | spreading | spreading to reflexed |
| Size of calyx in relation to fruit on secondary fruit | same size to larger | same size to larger | same size |
| Adherence of calyx | weak to medium | weak to medium | strong |
| Firmness of flesh | firm | soft to medium | firm |
| Evenness of flesh color | slightly uneven | slightly uneven | slightly uneven to even |
| Distribution of flesh color | marginal and central | marginal and central | marginal and central |
| Hollow center size | small | small | medium |
| Sweetness | strong | medium to strong | medium to strong |
| Texture when tasted | fine | fine to medium | medium |
| Acidity | medium | medium | medium |
| Time of flowering | late-February | early-March | early-March |
| Harvest Interval in 2002 | early-April thru early-November | mid-April thru early-November | mid-April thru early-November |
| Type of Bearing | partially everbearing | partially everbearing | partially everbearing |

5.3 STRESS PEST AND DISEASE RESISTANCE AND SUSCEPTIBILITY

TABLE 3

REACTIONS TO STRESS, PESTS, AND DISEASES FOR 'DRISCOLL CAMBRIA', 'SAN JUAN' AND 'ANA MARIA'

| | 'Driscoll Cambria' | 'Ana Maria' | 'San Juan' |
|---|---|---|---|
| Reaction to Stress | | | |
| high pH | moderately resistant | moderately resistant | moderately resistant |
| high soil salt levels | moderately resistant | moderately resistant | moderately resistant |
| Reaction to Pests | | | |
| *Tetranychus urticae* | moderately susceptible | susceptible | moderately susceptible |
| *Lygus hesperus* | susceptible | susceptible | susceptible |
| Reaction To Diseases | | | |
| Botrytis fruit rot | susceptible | susceptible | susceptible |
| Powdery mildew | susceptible | moderately susceptible | susceptible |
| Verticillium wilt | susceptible | susceptible | susceptible |
| Strawberry Mottic Virus | moderately resistant | moderately resistant | moderately resistant |
| *Xanthomonas fragariae* | moderately susceptible | moderately susceptible | moderately susceptible |

5.4 ISOZYME ANALYSIS

In addition to the morphological description above, the new cultivar 'Driscoll Cambria' has been analyzed to obtain an indication of its genetic makeup to provide further means for identifying the new variety and distinguishing it from some other somewhat similar and/or related strawberry varieties. Specifically, leaf samples of 'Driscoll Cambria', 'Ana Maria' and 'San Juan' were analyzed by electrophoresis for isozyme patterns of the enzymes phospoglucoisomerase (PGI), leucine aminopeptidase (LAP) and phosphoglucomutase (PGM), See *J. Amer. Soc. Hort. Sci.* 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL CAMBRIA', 'ANA MARIA' AND 'SAN JUAN'

| Locus | 'Driscoll Cambria' | 'Ana Maria' | 'San Juan' |
|---|---|---|---|
| PGI | A1 | A1 | A2 |
| LAP | B3 | B3 | B3 |
| PGM | C1 | C4 | C4 |

What is claimed is:

1. A new and distinct variety of strawberry plant, substantially as shown and described.

* * * * *